United States Patent [19]

Sullivan et al.

[11] 4,125,478

[45] Nov. 14, 1978

[54] AIR TREATING GEL EMPLOYING AMIDE POLYMER GELLING AGENT

[75] Inventors: Edward J. Sullivan; Giffin D. Jones, both of Midland, Mich.

[73] Assignee: The Dow Chemical Company, Midland, Mich.

[21] Appl. No.: 745,258

[22] Filed: Nov. 26, 1976

[51] Int. Cl.$^2$ .................... B01J 13/00; A61K 7/46; A61L 13/00
[52] U.S. Cl. .................... 252/316; 252/522; 424/76; 424/81
[58] Field of Search .................. 252/316, 522; 424/76, 424/81

[56] References Cited

U.S. PATENT DOCUMENTS

| | | | |
|---|---|---|---|
| 2,691,615 | 10/1954 | Turner et al. | 424/76 X |
| 2,927,055 | 3/1960 | Lanzet | 252/316 X |
| 3,244,640 | 4/1966 | Studt et al. | 252/316 |
| 3,767,787 | 10/1973 | Segal | 424/76 |

Primary Examiner—Richard D. Lovering

[57] ABSTRACT

A relatively dilute aqueous solution of an amide polymer such as polyacrylamide when treated with a small amount of a hypohalite salt solution reacts under ambient conditions to form a firm gel. Such firm gels are useful replacements for the aqueous gels prepared from vegetable gums and conventionally employed in air freshener devices and the like.

3 Claims, No Drawings

AIR TREATING GEL EMPLOYING AMIDE POLYMER GELLING AGENT

BACKGROUND OF THE INVENTION

This invention relates to improved air treating gels employing an aqueous gel of an amide polymer.

The use of aqueous gels in air freshener devices and the like is well known and is shown, for example, in U.S. Pat. Nos. 2,691,615 and 2,927,055. In such prior art devices, the gels have been described as consisting of over 90 percent, usually from 96 to 99 percent, of an aqueous medium. Of the aqueous medium, 1 to 10 percent comprises a plurality of volatile air treating components which are compatible, uniformly dispersible in water, and which normally volatilize slowly at room temperature, and 1 to 4 percent is a gelling agent. The amount of gelling agent present in proportion to the aqueous medium is such that the gel is firm and substantially free of syneresis. Heretofore, the gelling agents employed in such prior art gels have generally been vegetable gums such as agar-agar, carrageenan, locust bean gum and the like. These vegetable products present problems since they are natural products having nonuniform properties from batch to batch and since they must be prepared as hot solutions which must be gelled by cooling. Moreover, such vegetable products are subject to attack by microorganisms.

Therefore, it would be highly desirable to provide an air treating gel having a synthetic gelling agent which can be prepared with controlled properties from batch to batch and which does not require time consuming and expensive heating and cooling cycles.

SUMMARY OF THE INVENTION

Accordingly, the present invention is an improved air treating gel composition containing an ethylenically unsaturated amide polymer as an essential component of such a synthetic gelling agent. As the other essential component of the gelling agent, there is employed a gelling reactant capable of reacting with the amide polymer to form a firm gel as hereinafter defined. In the air treating gel composition, the gelling agent comprising the amide polymer and the gelling reactant is employed in an amount sufficient to gel the composition within a reasonable time at ambient conditions. In addition, the air treating gel composition comprises a predominant amount of an aqueous medium and a minor, air treating amount of at least one volatile air treating agent which is uniformly dispersible in water, normally volatilizes at room temperature and is compatible with the aforementioned gelling agent.

Embodiments of particular interest are those wherein the gelling agent comprises the aforementioned amide polymer and a hypohalite salt as the gelling reactant necessary to form the firm gel. In these particularly important embodiments, gelation of an aqueous solution of the gelling agent is advantageously carried out by combining an aqueous solution of the amide polymer and an amount of an aqueous hypohalite salt solution effective to react with the amide polymer under controlled conditions to form the desired aqueous gel composition. Most advantageously in the preparation of the air treating gel composition, the volatile air treating agent or agents are included in the afore-mentioned reaction mixture prior to the reaction to form the gel. Minor amounts of other additaments such as pigments, dyes or antimicrobial agents may be similarly incorporated in the composition as desired.

Surprisingly, in the practice of this invention, firm, nonweeping, aqueous gelled compositions are obtained in a highly reproducible manner. Moreover, the gelation reaction is initiated rapidly as soon as the amide polymer and the reactant are combined and proceeds readily under ambient conditions to form the firm gel.

The air treating aqueous gel compositions of the invention are particularly useful as air freshening devices, air disinfectants, deodorants, and the like.

DETAILED DESCRIPTION OF THE EMBODIMENTS

The amide polymers employed in the practice of this invention are addition polymers of ethylenically unsaturated amide monomers which may contain up to about 20 mole percent of another ethylenically unsaturated monomer copolymerizable with the amide monomer, provided that such other monomer is not reactive with the gelling reactant and provided further that the finished polymer contains no more than about 10 mole percent of organic acid moieties such as acrylic acid or methacrylic acid. So long as the amide polymer has sufficient molecular weight to react with the gelling reactant as defined hereinafter to form a desired firm gel, molecular weight of the amide polymer is not particularly critical. However, as a general rule amide polymers normally employed have weight average molecular weights varying from about 25,000 up to 2,000,000 or more with those having medium molecular weights in the range from about 100,000 to about 500,000 being preferred due to the ease of handling of such polymers. In practice, since the determination of molecular weights of such polymers is tedious and sometimes subject to uncertainties, it is convenient to characterize the polymers by a property related to molecular weight, namely the viscosity of an aqueous solution under specified conditions. Thus the preferred acrylamide polymers employed in the present invention are characterized by viscosities of from 1.2 to about 2.5 centipoises for an aqueous 0.5 percent by weight solution thereof in deionized water adjusted to a pH of 3.8 as determined with an Ostwald viscosimeter at a temperature of 25° C. Alternatively, commercial batches of aqueous 20 percent by weight solutions of polyacrylamides characterized by viscosities of from about 7,000 to about 100,000, as determined with a Brookfield Viscometer at 25° C., have been found useful in the invention.

In order that desired firm gels can be formed in accordance with the present invention, it is critical that the amide polymer be substantially free of substances which will react prematurely with the gelling reactant and thereby rendering it ineffective as a reactant in the desired gelation reaction. As an example, in the preferred embodiments when the reactant is a hypohalite salt, the amide polymers should be essentially free of acidic or strong reducing agents such as sulfites or bisulfites which are frequently added to such amide polymers either as cocatalysts in the polymerization or for the purposes of detoxifying residual monomer in the polymer. It is further necessary that the amide polymer solution be substantially free of chemicals, such as ammonia and amines, which react readily with organic isocyanate groups. It is also very desirable that the amide polymer have no more than about 10 mole percent of its carboxamide groups hydrolyzed to carboxylate groups. Preferably the amide polymer contains only three mole percent or less of such carboxylate groups with those containing one mole percent or less being especially preferred.

To form the desired firm gels, the amide polymer preferably contains from about 80 to 100 mole percent of one or more of the amide monomers, more preferably from about 90 to about 100 mole percent and most preferably from about 97 to 100 mole percent of amide monomers. Exemplary amide monomers include acrylamide, methacrylamide, fumaramide, ethacrylamide, N-(t-butyl)acrylamide, maleamide, citraconamide and the like. The amide monomer is preferably acrylamide or methacrylamide with acrylamide being most preferred. In any case, the monomer or mixture of monomers should be chosen so that the resulting polymer or copolymer is soluble in water. Thus, for example, the homopolymer of methacrylamide, being insoluble in water is unsuitable. However, copolymers of acrylamide with up to about 90 mole percent of methacrylamide may be employed.

Examples of other monomers which may be copolymerized with the aforementioned amide monomers include alkyl esters of $\alpha,\beta$-ethylenically unsaturated carboxylic acids such as ethyl acrylate, methyl acrylate, butyl acrylate and methyl methacrylate or monomers such as hydroxyethyl acrylate, sodium sulfoethyl acrylate, vinylbenzyl-trimethylammonium salts, sodium styrene-sulfonate, styrene, vinyltoluene and the like. Of course, it is understood that said other monomers should be chosen so that they do not react with the amide monomer or the gelling reactant or otherwise interfere with the gelation reaction.

For the purposes of this invention, a suitable gelling reactant is any one of several known reactants which will cause the amide polymer in aqueous solution to be converted to a firm gel under ambient conditions. For the purposes of this invention a firm gel is defined as a gel that holds the shape in which it is formed, that is, is self-supporting and does not flow under the force of gravity; such gels further should not show syneresis, that is, shrinkage with exudation of liquid. Preferably such gels should be characterized by a penetration reading of 15 millimeters or less in a Penetrometer test when performed as set forth in Example 3 below. Exemplary reactants suitable for the practice of this invention include inorganic hypohalite salts or a mixture of an organic hypohalite, such as tertiary butyl hypochlorite with an inorganic base. Of particular interest are the soluble hypohalite salts of metals and particularly of the alkali metals, preferably the hypochlorite or hypobromite salts, most preferably the hypochlorite salts. Examples of such hypochlorite and hypobromite salts are sodium hypochlorite, sodium hypobromite, potassium hypochlorite, calcium hypochlorite and potassium hypobromite. Other hypohalites such as tetramethylammonium hypochlorite can also be employed. In any case the hypohalite is employed in the presence of inorganic base as set forth hereinafter.

The volatile air treating agent suitably employed in the aqueous gel compositions of this invention may be any agent useful in the treating of air which is also compatible with (i.e., nonreactive with) the amide polymer and the gelling reactant and which is uniformly dispersible in water. For the purposes of this invention, the air treatment agent is considered uniformly dispersible in water if it is water soluble, inherently water dispersible (i.e., will disperse in water to form colloidal size particles without aid of a surfactant) or will disperse in water to form colloidal size particles with the aid of a surfactant. Preferably such volatile agents are either water soluble or inherently water dispersible. Such air treating agents are well known in the art. As a practical matter, essentially all volatile air treating agents employed in conventional air treating gels are suitable for the purposes of this invention. However, examples of some particularly beneficial air treating agents include: oil of lemon grass, oil of cedar wood, oil of Canadian fir, oil of pine, oil of wintergreen, aliphatic, especially monohydric, alcohols such as octanol; aliphatic aldehydes having from 2 to 20 carbon atoms particularly acetaldehyde, paraldehyde, 2-hexene-1-al, betahexylacrolein, phenyl-acetaldehyde, caproaldehyde, ethyl acrolein; bromals such as tribromoacetaldehyde, chlorals such as trichloroacetaldehyde and halogenated acetals; as well as esters such as amyl acetate, methyl salicylate and the like. Additional suitable volatile air treating agents are described in U.S. Pat. No. 2,691,615.

In the preparation of the air treating gel compositions of the present invention, it is generally desirable to combine an aqueous solution of the amide polymer with an aqueous solution or dispersion of the gelling reactant. The volatile air treating agent may be incorporated into one or the other aqueous solutions or dispersions prior to mixing to form the gel or simultaneous with such mixing. In some instances it may be desirable to incorporate the air treating agent in microencapsulated form to provide for slow release.

The concentration of the amide polymer to be employed will vary depending on the molecular weight of the polymer and the firmness of the gel desired. In general, the starting solution of the amide polymer advantageously contains from about 2 weight percent for very high molecular weight polymer to from about 4 to about 10 weight percent of the preferred medium molecular weight polymer. However, somewhat higher concentrations of the amide polymer, e.g., from about 10 to about 20 weight percent, may be employed when a relatively low molecular weight polymer is employed if the solution is substantially free of reducing agents such as sulfites, of toxic ingredients such as residual amide monomer and of competing chemicals such as ammonia or amines.

The amide polymers may be prepared by conventional, free radical-initiated, vinyl polymerization of the desired monomer in aqueous solution. In one method for preparing an aqueous solution of the amide polymer for use in this invention, an aqueous solution containing 20 weight percent of acrylamide or similar suitable amide monomer and sufficient cupric ions to inhibit premature polymerization of the amide monomer is heated to 35° C. and the pH of the resulting solution is adjusted to a value from about 4.5 to about 5, preferably about 4.6. To the aqueous solution of the amide monomer is added an aqueous solution of an EDTA-type chelating agent, such as Versene or Versenex chelating agent, in an amount sufficient to provide about 2 gram-moles of chelating agent per gram-atom of copper in the monomer solution. To this solution, a dilute solution of sodium persulfate in an amount from about 1800 to about 2100 parts per million parts of total monomer in the solution. Following the additon of persulfate, an aqueous solution of sodium bisulfite is added to provide the same amount of bisulfite as persulfate in the polymerization recipe. The addition of bisulfite initiates a rapid exothermic polymerization reaction. When the exotherm peaks, 500 parts of tertiary butyl hydroperoxide per million parts of monomer is added to the reaction mixture and the latter is heated to 90° C. for 1 hour to remove residual bisulfite and monomer. Thereafter the solution is cooled to 30° C. or below for storage. In applications where amide polymers may be contacted by humans repeatedly, it is desirable that the polymer contain no more than about 0.5 weight percent, preferably less than 0.01 weight percent of residual amide monomer.

When the gelling reactant is the preferred hypohalite salt in the form of an aqueous solution thereof, the aqueous solution of the hypohalite salt contains from about 1 to about 10 percent of the hypohalite salt and is employed in an amount to provide from about 0.02 to about 0.08 mole of hypohalite per mole of amide monomer combined in the polymer. Preferably to prepare a firm gel particularly beneficial in air freshener devices, an aqueous solution containing from about 4 to about 10, most preferably from about 4 to about 8 weight percent of amide polymer having a number average molecular weight in the range from 100,000 to 500,000 is combined with, by adding thereto with thorough mixing, an aqueous solution containing from about 5 to about 6 weight percent of hypochlorite salt such as sodium hypochlorite in an amount sufficient to provide about 0.04 mole of hypochlorite per mole of amide monomer combined in said polymer.

The hypohalite solutions, which are of particular interest as gelling reactants in the practice of this invention, are readily prepared by dissolving the corresponding free halogen in a slight molar excess of alkali metal hydroxide with cooling to prevent the formation of halites or halates. As a result of this preferred practice, a solution is made which contains a mole of halide ion for each mole of hypohalite ion formed. A slight excess of alkali metal hydroxide is employed to stabilize the solution and to provide an aqueous solution of hypohalite having a pH of at least about 12 and preferably a pH over 13 without containing such an excess of alkali as to cause undesired hydrolysis of the amide groups of the polymer when the hypohalite solution is mixed with the amide polymer solution. For economical reasons, it is desirable to employ a commercial household bleach which is an aqueous solution containing about 5.25 to 5.5 weight percent of sodium hypochlorite, an approximately equimolar proportion of sodium chloride and sufficient excess of sodium hydroxide to provide a solution havng a pH of 13.5 or slightly higher. In commercial bleach the stabilizing excess of NaOH corresponds to about 0.3 to 1 percent by weight of the solution.

Firm gels, as defined hereinbefore, are readily formed when, in addition to the aforementioned aqueous gelling agent, inert pigments and/or volatile air treating agent such as odorants or odor masking agents compatible with water and the aqueous gel agent are incorporated into the aqueous amide polymer solution prior to gelation. If the conventional volatile odorants such as essential oils are to be incorporated into the polymer solution, it is desirable to employ compatible carriers such as ethylene glycol since the lower aliphatic alcohols may cause local precipitation of the amide polymer. Alternatively, the essential oils may be mixed with a small amount of a compatible surfactant, preferably a nonionic surfactant, such as a polyoxyethylated derivative of an alkyl phenol (Triton X-100), to aid in the dispersing of the essential oils in the polymer solution.

In any case, to prepare an air treating gel, it is desirable to disperse the volatile air treating agent or mixture of several air treating agents in an amount from about 1 to about 10 weight percent in an aqueous solution of amide polymer containing the aforementioned amounts, preferably from about 4 to about 8 weight percent, of the polymer, and then add a desired amount of hypohalite salt, usually as an aqueous solution as defined above, and pour the resulting mixture into suitable molds or containers. If, however, the volatile air treating agent or agents are sensitive to oxidants such as the hypohalite salts, it is preferred to mix the polymer solution and hypohalite solution and then quickly disperse the air treating agent in the mixture and pour into molds before gelation is complete.

In the practice of this invention as in the practice of the subject matter described in U.S. Pat. No. 2,927,055, it is often desirable to employ a mixture of air treating agents as disclosed therein which normally volatilize at different rates at a given temperature near ambient temperature. Accordingly, the mixtures of air treating agents described in said patent are particularly useful in the practice of the present invention.

In the practice of the preferred embodiments of the present invention, the resulting aqueous gel composition comprises from about 2 to about 10, most preferably from about 5 to about 8, weight percent of the aqueous gelling agent (i.e., combined amide polymer and hypohalite salt), from about 1 to about 10, most preferably from about 1 to about 4, weight percent of the volatile air treating agent and a remaining amount usually at least 80 weight percent, most preferably from about 88 to about 92 weight percent of an aqueous medium. It is of course understood that other additaments such as pigments, antimicrobial agents and the like commonly employed in conventional air treating agents are optionally included in the aforementioned preferred compositions.

The following examples are given to illustrate the invention and should not be construed as limiting its scope. Unless otherwise indicated all parts and percentages in the following examples are by weight.

EXAMPLE 1

An aqueous 20 percent solution of a polyacrylamide, substantially free of sulfite or bisulfite and having a viscosity of 13,700 centipoises as determined with a Brookfield LVT viscometer employing spindle No. 4 at 30 revolutions per minute at 25° C., is diluted with deionized water to a concentration of 8 percent. A 150 milliliter portion of the resulting solution is mixed rapidly with 40 milliliters of water and 9.6 milliliters of aqueous 5.3 percent solution of sodium hypochlorite with stirring. The resulting mixture sets to a firm, continuous self-supporting structure in about 5 minutes at room temperature. The gel product does not exude water by syneresis when stored without exposure to air currents. When exposed to air the gel loses water by evaporation and shrinks gradually without exuding liquid. The polyacrylamide in this example contains 0.01 percent or less of residual monomer and has less than 1 percent of its amide groups hydrolyzed to carboxyl groups.

A gel having properties similar to those in the preceding paragraph is prepared by following the procedure set forth in the preceding paragraph except that about 4 milliliters of a commercial mixture of essential oils having a floral fragrance is dispersed in the 40 milliliters of water with the aid of a drop of nonionic surfactant prior to mixing with the amide polymer solution and the solution of sodium hypochlorite. In addition the resulting gel exhibits air treating capabilities at least as effective as those of commercially available air freshening gels.

EXAMPLE 2

Following the general procedure of Example 1 the polyacrylamide solution of Example 1 is diluted to provide a series of solutions containing 4, 5, 6 or 7 percent, respectively, of the polymer. Commercial household bleach containing about 5.25 percent by weight of sodium hypochloride is mixed with each of the polymer solutions in the amount of 0.8 milliliter per gram of polymer. In each case a self-supporting gel is formed in 20 minutes or less at room temperature.

Similar gels are formed when volatile air treating agents compatible with water such as pine oil, cedarwood oil or mixtures such as are shown in U.S. Pat. No. 2,927,055 are incorporated into the starting polymer solution or diluting water prior to gellation.

EXAMPLE 3

A series of aqueous polyacrylamide solutions are obtained in which all polymers (1) have less than 1 mole percent of their amide groups hydrolyzed to carboxyl groups, (2) are substantially free of sulfite or bisulfite, and (3) have residual monomer contents less than 0.5 percent based on the polymer as a result of post-polymerization treatment with tertiary butyl hydroperoxide at 90° C. for about 1 hour. The polymers have molecular weights ranging up to about 500,000 as evidenced by viscosities of the aqeuous 20 percent solutions thereof being in the range from about 7,000 to about 86,000 cps using the Brookfield viscometer under the conditions described in Example 1. A portion of each polymer solution is diluted with deionized water to provide a series of solutions each containing 5 percent of amide polymer and then subjected to the following procedure.

A 200-milliliter portion of 5 percent polymer solution is mixed with 5 milliliters of household bleach (aqueous 5.5 percent sodium hypochlorite solution having a pH of about 13.8). A 165-gram portion of the resulting mixture is poured into an expanded polystyrene foam cup. The mixture gels within a few minutes and is allowed to age in the cup for 24 hours during which time no syneresis is observed. The cup is cut away to provide a truncated cone of gel measuring 73 millimeters in height, 68 millimeters on the larger diameter and 43 millimeters on the smaller diameter. The gel is placed on the larger diameter base in a Penetrometer equipped with a 45° aluminum cone weighing 26.513 grams, to which no extra weight is added. The penetration of the aluminum cone into the gel is measured after one minute; the penetrometer is a "Precision Penetrometer" manufactured by Precision Scientific Company of Chicago, Ill. The results are summarized in the following table wherein the polyacrylamide polymers are characterized by the viscosity in centipoises of the solution thereof at the indicated concentrations as determined with a Brookfield LVT viscometer using the No. 4 spindle at the indicated revolutions per minute.

TABLE

| Sample No. | Polymer Concentration, weight percent | Viscosity cps. | Penetration mm. |
| --- | --- | --- | --- |
| 1 | 20.0 | 7,000 (30 rpm) | 11.0 |
| 2 | 20.0 | 13,700 (30 rpm) | 14.6 |
| 3 | 21.1 | 18,000 (30 rpm) | 13.6 |
| 4 | 21.2 | 86,000 ( 6 rpm) | 14.1 |

As evidenced by the foregoing data of the table, strong gels are obtained in all cases and the strength of the gel is not influenced appreciably by substantial differences in the molecular weight of the polymer.

What is claimed is:

1. In an air treating, gelable composition which composition comprises at least one volatile air treating agent and an aqueous gelling agent dispersed therein, the improvement wherein the gelling agent comprises (1) a polymer containing at least 80 mole percent of combined ethylenically unsaturated amide monomer, said polymer being substantially free of sulfite and bisulfite ions and (2) a hypohalite salt gelling reactant for said polymer, the hypohalite salt being employed as a solution having a pH at least about 12; the polymer and the reactant being present in proportions in the gelable composition to provide a firm aqueous gel medium.

2. The firm aqueous gel medium of claim 1 containing a preponderance of water and containing an air treating amount of at least one volatile air treating agent dispersed therein wherein the gel medium is prepared by admixing an aqueous solution containing from about 2 to about 10 weight percent of the amide polymer with sufficient aqueous solution of an alkali metal hypohalite, having a pH of at least 12, to provide from about 0.02 to about 0.08 mole of hypohalite per mole of amide polymer in the mixture.

3. The gel medium of claim 1 wherein the gel medium is prepared by admixing an aqueous solution containing from about 4 to about 8 weight percent of a polyacrylamide, substantially free of sulfite or bisulfite and containing less than 0.01 percent of residual acrylamide monomer and having less than 6 mole percent of its carboxamide groups hydrolyzed to carboxylate groups, with an amount of an aqueous solution containing from about 5 to about 6 weight percent of sodium hypochlorite and having a pH of about 12 to about 13.5, said hypochlorite being present in an amount sufficient to provide about 0.04 mole of hypochlorite per mole of acrylamide combined in the polyacrylamide.

* * * * *